United States Patent [19]

Coverdale et al.

[11] 4,057,633
[45] Nov. 8, 1977

[54] COMPOSITIONS AND METHOD OF USING QUINOLYLAMINOBENZOYLPIPERAZINO-1-OXIDES

[75] Inventors: Charles E. Coverdale, Portage; Louis L. Skaletzky, Kalamazoo, both of Mich.

[73] Assignee: The Upjohn Company, Kalamazoo, Mich.

[21] Appl. No.: 715,229

[22] Filed: Aug. 18, 1976

Related U.S. Application Data

[60] Division of Ser. No. 508,790, Sept. 23, 1974, Pat. No. 3,992,382, which is a continuation-in-part of Ser. No. 370,341, June 15, 1973, abandoned.

[51] Int. Cl.² ............................................. A61K 31/495
[52] U.S. Cl. .................................................... 424/250
[58] Field of Search ......................................... 424/250

[56] References Cited

U.S. PATENT DOCUMENTS 3,632,761    1/1972    Graham et al. ...................... 424/248

Primary Examiner—Frederick E. Waddell

Attorney, Agent, or Firm—William G. Jameson; Sidney B. Williams, Jr.

[57] ABSTRACT

Novel compounds of the formula:

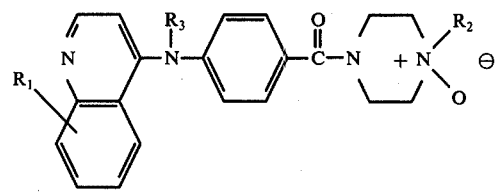

are disclosed with the corresponding hydrates and pharamceutically acceptable acid addition salts thereof, wherein $R_1$ is halogen, lower alkyl, or trifluoromethyl; $R_2$ is lower alkyl, substituted or unsubstituted phenyl or benzyl and $R_3$ is hydrogen. The novel compounds are useful for the treatment of hypertension and anxiety in mammals, including humans.

Disclosed also are compositions containing the novel compounds of the invention and methods of their use in the treatment of hypertension and anxiety.

9 Claims, No Drawings

COMPOSITIONS AND METHOD OF USING QUINOLYLAMINOBENZOYLPIPERAZINO-1-OXIDES

CROSS REFERENCES TO RELATED APPLICATIONS

This is a division of application Ser. No. 508,790, filed Sept. 23, 1974, now U.S. Pat. 3,992,382, which is a continuation-in-part of application Ser. No. 370,341, filed June 15, 1973, now abandoned.

BACKGROUND OF THE INVENTION

1. Field of the Invention.

The invention concerns novel quinolylaminobenzoyl-piperazine-1-oxides, hydrates thereof and pharmaceutically acceptable acid addition salts thereof; compositions prepared therefrom and methods of their use.

2. Description of the Prior Art.

Prior hereto, 4-alkyl- and 4-benzyl-1-[p-[[(trihalomethyl)-4-quinolyl]amino]benzoyl]piperazines were known as was their use as antihypertensives; see for example British Patent 1,268,469. Such compounds are starting compounds for the preparation of the corresponding N-oxides of this invention.

U.S. Pat. No. 3,632,761 describes a number of 4-alkyl- and 4-benzyl-1-[p-[(4-quinolyl)amino]benzoyl[piperazines and their use as antihypertensives. These latter compounds are also starting compounds for the preparation of the corresponding compounds of our invention.

U.S. Pat. No. 3,136,769 discloses a number of 4-amino-quinoline-1-oxides and their use as antiparasitic agents.

Prior hereto, it was generally accepted that the N-oxides were distinctly different chemical entities from the corresponding non-oxide compounds. In general, the N-oxides and the analogous non-oxides were thought to share few properties in common. It was, therefore, surprising to find that the N-oxides of our invention possess properties which make them useful as antihypertensive agents, sharing this property with the non-oxide analogs. An advantage found in the N-oxide compounds of our invention is their improved aqueous solubility over the parent compounds, making them useful in a wider variety of pharmaceutical preparations and uses.

SUMMARY OF THE INVENTION

The invention comprises compounds of the formula:

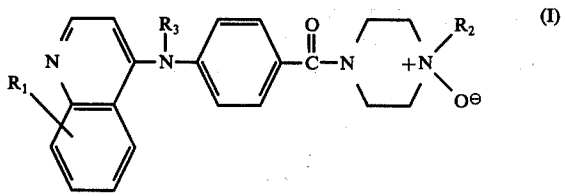

hydrates thereof and pharmaceutically acceptable acid addition salts thereof wherein $R_1$ is halogen, lower alkyl, or trifluoromethyl; $R_2$ is selected from lower alkyl, benzyl, phenyl and phenyl substituted with one of the groups selected from halogen, lower alkyl, and trifluoromethyl; $R_2$ is hydrogen.

The term "lower alkyl" is used herein in its conventionally accepted sense as meaning a saturated hydrocarbon from which a hydrogen atom has been removed. Illustrative of lower alkyl are the monovalent groups obtained upon removal of a hydrogen atom from a saturated hydrocarbon having from 1 to 4 carbon atoms, inclusive. Examples of such monovalent groups are methyl, ethyl, propyl, butyl and isomeric forms thereof.

The terms "halogen" and "halo" are employed in their usually accepted sense as being embracive of bromine, chlorine, iodine and fluorine, and bromo, chloro, iodo and fluoro, respectively.

The term "phenyl substituted with one of the groups selected from halogen, lower alkyl, and trifluoromethyl" means phenyl in which one of the hydrogen atoms has been replaced with a group selected from halogen, lower alkyl, and trifluoromethyl as previously defined.

The compounds (I) of the invention, hydrates thereof and the pharmaceutically acceptable acid addition salts thereof are useful for treating mammals, including humans, for hypertension and anxiety. Preferred compounds (I) for the treatment of hypertension are those wherein $R_1$ is trifluoromethyl, $R_2$ is lower alkyl and $R_3$ is hydrogen.

The invention also comprises pharmaceutical preparations containing compounds (I) of the invention, hydrates and pharmaceutically acceptable acid addition salts thereof as the essential active ingredient and methods of using them for the treatment of hypertension in mammals, including humans.

DETAILED DESCRIPTION OF THE INVENTION

The compounds (I) of the invention are prepared by N-oxidation of the corresponding compounds (II), employing hydrogen peroxide or a percarboxylic acid which can supply an oxygen atom with 6 electrons. The reaction is well known and using hydrogen peroxide as the oxidizing agent may be illustrated by the schematic formula:

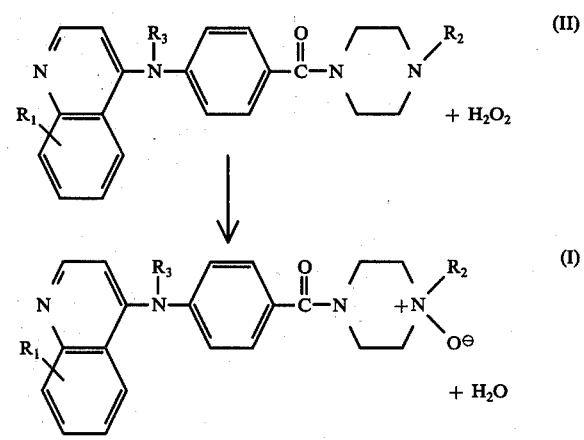

The preparation of the compounds (I) is carried out by admixture of the reactants (II) with the oxidizing agent in substantially equimolar proportions. Preferably a 10 to 25 molar excess of the oxidizing agent is employed.

Although the oxidation illustrated above is readily carried out over a broad range of temperature conditions, i.e., from about 10° C. to about 60° C., it is preferably carried out at ambient temperatures (circa 25° C.).

Advantageously the above described oxidation reaction is carried out in the presence of an inert organic solvent for reactant (II). An inert organic solvent is one which does not enter into reaction with the reactants (II) or the oxidizing agents or in any way alter the desired course of the reaction. Illustrative of inert organic solvents are methanol, ethanol, propanol, butanol, pentanol, hexanol, cyclohexanol, n-hexane, benzene, toluene, xylene, and like organic solvents. The quantity of solvent employed is not critical. In general, sufficient solvent is employed to solubilize the reactant (II).

Completion of the oxidation reaction may be ascertained by conventional analytical methods. For example, the disappearance of starting reactant (II) and appearance of the desired oxide product (I) may be ascertained by thin-layer chromatography.

Upon completion of the reaction, the desired compounds (I) are readily separated from the reaction mixture by conventional methods. For example, the excess oxidation agent is removed by conventional techniques and the compounds (I) separated by solvent extraction and crystallization.

The compounds (I) of the invention are generally hygroscopic, and readily form hydrates upon exposure to water. Generally the average amount of water held by a mole of the compound (I) is from about 0.01 moles to about 1.0 moles. The hydrates may be used for the same purposes as the dehydrate form. The dehydrate, when desired, may be prepared from the hydrated forms by conventional methods of drying and are stable when stored under anhydrous conditions.

The starting compounds of formula (II) wherein $R_2$ is lower alkyl or benzyl are generally well-known compounds as is their preparation; see for example U.S. Pat. No. 3,632,761 and British Pat. No. 1,268,469 and the references cited by these patents.

Illustrative of the compounds (11) wherein $R_2$ is lower alkyl or benzyl are 1-[p-[(4-quinolyl)amino]benzoyl]-4-methylpiperazine; 1-[p-[(7-chloro-4-quinolyl)amino]benzoyl]-4-methylpiperazine; 1-[p-[(7-chloro-4-quinolyl)amino]-benzoyl]-4-butylpiperazine; 1-[p-[(7-chloro-4-quinolyl)-amino]benzoyl]-4-benzylpiperazine; 1-[p-[(6-methoxy-4-quinolyl)amino]benzoyl]-4-methylpiperazine; 1-[p-[(5-isobutoxy-4-quinolyl)amino]benzoyl]-4-methylpiperazine; 1-[p-[(7-methyl-4-quinolyl)amino]benzoyl]-4-methylpiperazine, 1-[p-[(6-isopropyl-4-quinolyl)amino]benzoyl]-4-methylpiperazine, 1-[p-[(7-cholor-4-quinolyl)-N-ethylamino]benzoyl]-4-methylpiperazine and like compounds, all of which may be prepared according to the method set forth in U.S. Pat. No. 3,632,761; 1-[p-[[(7-trifluoromethyl)-4-quinolyl]amino]benzoly]-4-methylpiperazine; 1-[p-[[(7-trifluoromethyl)-4-quinolyl]-amino]benzoyl]-4-isobutylpiperazine; 1-[p-[[(7-trifluoromethyl)-4-quinolyl]-amino]benzoyl]-4-benzylpiperazine; 1-[p-[[(7-trichloromethyl)-4-quinolyl]amino]benzoyl]-4-methylpiperazine and like compounds which may be prepared according to the method set forth in British Pat. No. 1,268,469.

Those compounds of the formula (II) wherein $R_2$ is phenyl or phenyl substituted with a group selected from halogen, lower alkyl, lower alkoxy and trihalomethyl are novel compounds. They may be prepared by reacting a 4-chloroquinoline of the formula:

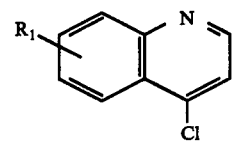

wherein $R_1$ is as defined above with a p-aminobenzamide of formula:

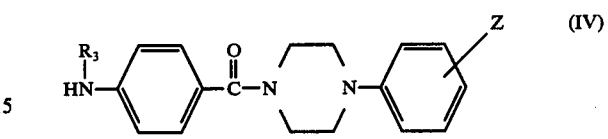

wherein $R_3$ is as defined above and Z is hydrogen, halogen, lower alkyl or trifluoromethyl.

The above described reaction is carried out by conventional methods of reacting 4-chloroquinolines with amines, for example, the method of Morley et al., J. Chem. Soc., 1014 (1949) or alternatively the method of Banks, J. Amer. Chem. Soc., 66. 1127 (1944).

4-Chloroquinolines of the formula (III) are well known: see for example U.S. Pat. No. 3,632,761; British Pat. No. 1,268,469 and Morley et al., supra.

Illustrative of the 4-cholorquinolines (III) are 4-chloroquinoline, 4,7-dichloroquinoline, 7-oromo-4-chloroquinoline, 8-fluoro-4-chloroquinoline, 7-methyl-4-chloroquinoline, 7-butyl-4-chloroquinoline, 4-chloro-6-isopropylquinoline, 4-chloro-5-methoxyquinoline, 4-chloro-7-trifluoromethylquinoline, 4-chloro-7-trichloromethylquinoline and the like.

The p-aminobenzamides (IV) wherein $R_3$ is hydrogen may be prepared by first condensing p-nitrobenzoyl chloride with an appropriate N-substituted piperazine of formula:

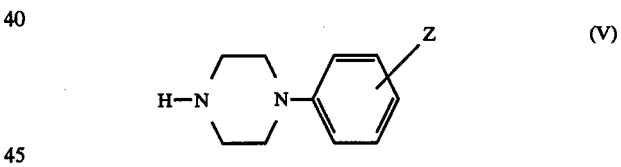

wherein Z is as defined above and then reducing the nitro product thereby obtained by catalytic hydrogenation. The technique is well known; see for example Moore et al., J. Chem. Soc., 1929, 39 describing such a condensation and Augustine, Catalytic Hydrogenation, Marcel Delsker, N.Y., 1965, pp. 91–102 for a discussion of methods of reducing the nitro group.

The starting compounds (V) are readily prepared by condensing the appropriate aniline of formula:

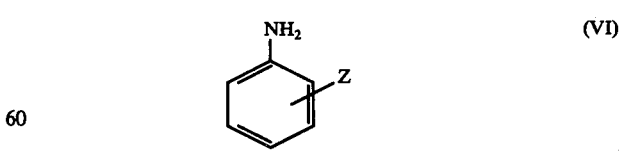

wherein Z is as defined above, with diethanolamine [method of Pollard et al., J. Amer. Chem. Soc., 56, 2199 (1934)]. Anilines of formula (VI) are well known and are represented for example by aniline, p-chloroaniline, m-methylaniline, m-methoxyaniline, p-trichloromethylaniline and the like.

The p-aminobenzamides (IV) wherein $R_3$ is lower alkyl are prepared by alkylation of the corresponding compound (IV) wherein $R_3$ is hydrogen. The procedure is well known, and comprises for example, reacting the compound (IV) wherein $R_3$ is hydrogen with a stoichiometric proportion of trifluoroacetic anhydride to obtain the corresponding N-trifluoroacetyl amine. The product of the reaction is then alkylated with an appropriate dialkyl sulfate alkylating agent and hydrolyzed to remove the N-trifluoroacetyl group. The procedure is well known, and complete details of such an alkylation are disclosed for example by Johnstone et al., J. Chem. Soc., C, 2223 (1969).

The compounds (I) of the invention can exist in either the free base form or in the form of a mono-or di-acid addition salt. The acid addition salts are prepared by reacting the free base (I) with a stoichiometric proportion of an appropriate acid such as hydrochloric acid. The method is well known to those skilled in the art, and may be carried out in aqueous or non-aqueous media such as ethanol, ether, ethyl acetate and the like.

The pharmaceutically acceptable acid addition salts may be used for the same purposes as the free base. Illustrative of pharmaceutically acceptable acid addition salts are those formed upon reaction of the compounds (I) of the invention with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid, and the like.

This invention relates also to pharmaceutical dosage unit forms for systemic administration (oral and parenteral administration) which are useful in treating hypertension and anxiety in mammals, including humans. The term "dosage unit form" as used in this specification and in the claims refers to physically discrete units suitable as unitary dosages for mammalian subjects, each unit containing a predetermined quantity of the essential active ingredient, i.e., a compound (I) or a hydrate or a pharmaceutically acceptable acid addition salt thereof, calculated to produce the desired effect in combination with the required pharmaceutical means which adapt said ingredient for systemic administration. Examples of dosage unit forms in accordance with this invention are tablets, capsules, orally administered liquid preparations in liquid vehicles, sterile preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid pharmaceutical preparations for oral administration are prepared in water or aqueous solutions which advantageously contain suspending agents, such as for example, sodium carboxymethylcellulose, methylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferably to include isotonic agents, for example, sugars or sodium chloride. Carriers and vehicles include vegetable oils, water, ethanol, and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as for example, ethylene oxide. The aforesaid carries, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 10 mg. to about 500 mg. of the essential active ingredient per dosage unit form. The amount of the essential active ingredient provided in the pharmaceutical dosage unit forms is based on our finding that the effective amount of compounds (I) of the invention, acid addition salts and hydrates thereof, for obtaining a hypotensive effect in mammals is within a range from about 0.1 mg. per kg. to about 50 mg. per kg. of body weight of the recipient, daily. Preferably 0.5 mg./kg. to about 25 mg./kg. daily is provided.

Advantageously the compounds of the invention (I), hydrates and pharmaceutically acceptable acid addition salts thereof may also be combined with sedatives and tranquilizers such as phenobarbital, pentobarbital, chloral hydrate, chlorpromazine, thioridazine and the like when sedation or tranquilization of the mammal being treated is also desired.

Combinations with other antihypertensive agents such hydralazine hydrochloride, hexamethonium bromide, mecamylamine hydrochloride, phenoxybenzamine hydrochloride, quanethidine sulfate, methyldopa and the like may be advantageous in overcoming developing tolerance or "resistance" to such agents.

Combinations with antidepressant agents such as d-amphetamine, pheniprazine hydrochloride, tranylcypromine, imipramine, desipramine, amitriptyline, nortriptyline, protriptyline and methylphenidate hydrochloride may be made when desired.

Combinations with diuretic agents such as ethoxzolamide, hydrochlorothiazide, trichlormethiazide, acetazolamide, chlorthalidone, triamterene, quinethazone, cyclothiazide, chlorothiazide, benzthiazide and the like may also be advantageous for the treatmen of hypertension.

Illustrative of unit dose forms of the invention containing additional active ingredients incorporated in the present pharmaceutical dosage unit forms with an effective amount of a compound (I) of the invention, or a hydrate or acid addition salt thereof, are other active ingredients such as, for example, antihypertensive and diuretic agents such as reserpine (0.05 to 1 mg.), hydralazine (10 to 100 mg.), methyldopa (100 to 250 mg.), guanethidine (10 to 50 mg.), hydrochlorothiazide (15 to 50 mg.), or ethoxzolamide (50 to 150 mg.); tranquilizers, anti-psychotic and anti-anxiety agents such as chlorpromazine (5 to 50 mg.), thioridazine (5 to 100 mg.), haloperidol (0.5 to 5 mg.), meprobamate (100 to 400 mg.), chlordiazepoxide (5 to 50 mg.), diazepam (2 to 15 mg.), and ectylurea (100 to 300 mg.); barbiturates such as phenobarbital (8 to 60 mg.), butabarbital (8 to 60 mg.), and amobarbital (16 to 120 mg.); analgesics such as aspirin (150 to 600 mg.) and acetaminophen (150 to 600 mg.); and antidepressants such as amitriptyline hydrochloride (10 to 50 mg.), methylphenidate hydrochloride (5 to 20 mg.), d-amphetamine sulfate (2 to 15 mg.), methamphetamine hydrochloride (2 to 15 mg.) and melitracen (15 to 50 mg.).

The following examples describe the manner and process of making and using the invention and set forth the best mode contemplated by the inventors of carrying out the invention but are not to be construed as limiting.

EXAMPLE 1

To a solution of 1.3 ml. of 30 percent hydrogen peroxide in water there is added 25 ml. of methanol. The resulting mixture is admixed with 0.3 gms. (0.00079 moles) of 1-[p-[(7-chloro-4-quinolyl)amino]benzoyl]-4-methylpiperazine (Preparation 1., of U.S. Pat. No. 3,632,761) and the resulting mixture allowed to stand at room temperature for 3 days. At the end of this period, 1 ml. of 30 percent hydrogen peroxide in water is added and the resulting mixture allowed to stand at room temperature for 2 days. At the end of this period excess hydrogen peroxide in the reaction mixture is decomposed by adding with stirring under a nitrogen gas atmosphere and initial cooling in ice bath, added an alcoholic suspension of about 0.20 gms. of 5 percent platinum on carbon. This mixture is stirred overnight, filtered and the filtrate concentrated under vacuum. The concentrated filtrate is dissolved in a mixture of isopropanol-ether-Skellysolve B* (*essentially n-hexane, b.p. 60° C.-68° C., Skelly Oil Co.), and solvent is stripped until a crystalline precipitate appears. The precipitate is separated by filtration and recrystallized from isopropanol-ether and dried to give 125 mg. (40 percent of theory) of 1-[p-[(7-chloro-4-quinolyl)amino]-benzoyl]-4-methylpiperazine-4-oxide.

Structure of the product is confirmed by elemental analysis, infra-red spectral analysis and nuclear magnetic resonance analysis.

Similarly, following the above procedure but replacing the 1-[p-[(7-chloro-4-quinolyl)amino]benzoyl]-4-methylpiperazine as used therein with an equal molar proportion of 1-[p-[(4-quinolyl)amino]benzoyl]-4-methylpiperazine; 1-[p-[(7-chloro-4-quinolyl)amino]-benzoyl]-4-butylpiperazine; 1-[p-[(7-chloro-4-quinolyl)amino]benzoyl]-4-benzylpiperazine; 1-[p-[(6-methoxy-4-quinolyl)amino]benzoyl]-4-methylpiperazine; 1-[p-[(5-isobutoxy-4-quinolyl)amino]benzoyly]-4-methylpiperazine; 1-[p-[(7-methyl-4-quinloyl)amino]benzoyl]-4-methylpiperazine; 1[p-[(6-isopropyl-4-quinolyl)amino]-benzoyl]-4-methylpiperazine; 1-[p-[[(7-trifluoromethyl)-4-quinolyl]amino]benzoly]-4-isobutylpiperazine; 1-[p-[[(7-trifluoromethyl)-4-quinolyl]amino]benzoyl]-4-benzylpiperazine; 1-[p-[[(7-trichloromethyl)-4-quinolyl]-amino]benzoyl]-4-methylpiperazine; and 1-[p-[(7-chloro-4-quinolyl) N-ethylamino]benzoyl]-4-methylpiperazine, respectively, there is obtained 1-[p-[(4-quinolyl)amino]benzoyl]-4-methylpiperazine-4-oxide; 1-[p-[(7-chloro-4quinolyl)amino]benzoyl]-4-butylpiperazine-4-oxide; 1-[p-[(7-chloro-4-quinolyl)amino]benzoyl]-4-benzylpiperazine-4-oxide; 1-[p-[(6-methoxy-4-quinolyl)amino]amino]benzoly]-4-methylpiperazine-4-oxide; 1-[p-[(5-isobutoxy-4-quinolyl)amino]benzolyl]-4-methylpiperazine-4-oxide; 1-[p-[(7-methyl-4-quinolyl)amino]benzoly]-4-methylpiperazine-4-oxide; 1-[p-[(6-ispropyl-4-quinolyl)- amino]benzoyl]-4-methylpiperazine-4-oxide; 1-[p-[[(7-trifluoromethyl)-4-quinolyl]-amino]benzoyl]-4-isobutypiperazine-4-oxide; 1-[p-[[(7-trifluoromethyl)-4-quinolyl]amino]-benzoyl]-4-benzyl-piperazine-4-oxide; 1-[-[[(7-trichloromethyl)-4-quinolyl]amino]benzoly]-4-methylpiperazine-4-oxide; and 1-[p-[(7-chloro-4-quinolyl)-N-ethylamino]benzoly]-4-methylpiperazine-4-oxide, respectively.

Similary, following the procedure of Example 1 above but replacing the 1-[p-[(7-chloro-4-quinolyl)amino]benzoyl]-4-methylpiperazine as used therein with 1-[p-[(7-chloro-4-quinolyl)amino]benzoly]-4-phenylpiperazine; 1-[p-[(7-chloro-4-quinolyl)amino]-benzoyl]-4-(p-chlorophenyl)piperazine; 1-[p-[(7-chloro-4-quinolyl)amino]benzoyl]-4(m-methoxyphenyl)piperazine; 1-[p-[(7-chloro-4-quinolyl)amino]benzoly]-4-(o-tolyl)piperazine; and 1-[p-[(7-chloro-4-quinolyl)amino]-benzoyl]-4-(m-trifluoromethylphenyl)piperazine, respectively, all of which may be prepared by reacting 4,7-dichloroquinoline with an appropriate p-aminobenzamide of formula (IV), supra. according to the method of Morley et al., supra., there is obtained the corresponding 1-[p-[(7-chloro-4-quinolyl)amino]benzoyl]-4-phenylpiperazine-4-oxide; 1-[p-[(7-chloro-4-qunriolyl)amino]benzoly]-4-chlorophenyl)-piperazine-4-oxide; 1-[p-[(7-chloro-4-quinolyl)amino]benzoyl]-4-(m-methoxyphenyl)piperazine-4-oxide; 1-[p-[(7-chloro-4-quinolyl)amino]benzoyl]-4-(o-tolyl)piperazine-4-oxide; and 1-[p-[(7-chloro-4-quinolyl)amino]benzoyl]-4-(m-trifluoromethylphenyl)piperazine-4-oxide, respectively.

EXAMPLE 2

To a solution of 2.0 ml. of 30 percent hydrogen peroxide in water there is added 20 ml. of methanol. The resulting mixture is admixed with 0.30 gms. (0.000725 moles) of 1-[p-[[(7-trifluoromethyl)-4-quinolyl]amino]-benzoly]-4-methylpiperazine (prepared according to the method of Example 1, British Pat. No. 1,268,469). The mixture obtained is allowed to stand at room temperature for 5 days. At the end of this period, excess hydrogen peroxide is separated by first cooling the mixture last obtained in an ice bath and then adding 0.2 gms. of 5 percent platinum on carbon under a nitrogen gas atmosphere. After standing overnight, the reaction mixture is filtered and the filtrate concentrated under vacuum. The concentrate is dissolved in a mixture of isopropanol-ether and the solution concentrated until a precipitate occurs. The precipitate is separated and dried to give 1-[p-[[(7-trifluoromethyl)-4-quinolyl]-amino]benzoyl]-4-methylpiperazine-4-oxide hydrate.

EXAMPLE 3

1-[p-[(7chloro-4-quinolyl)amino]benzoyl]-4-methyl-piperazine-4-oxide (Example 1, supra.) and a mixture of hydrochloric acid in ethanol are admixed together, in proportions such that the molar proportion of acid is twice the molar proportion of the oxide reactant. The reaction mixture is evaporated to dryness under reduced atmospheric pressure and the residue recrystallized from ethanol to give 1-[p-[(7-chloro-4-quinolyl)amino]benzoly]-4-methylpiperazine-4-oxide dihydrochloride.

The following examples illustrate the compositions and uses of the compounds of the invention. In each of Examples 4 through 13, infra., the term "essential active ingredient" has been employed for convenience to mean 1-[p-[(7-chloro-4-quinolyl)amino]benzoyl]-4-methylpiperazine-4-oxide (Example 1, supra.) as illustrative of the compounds (I).

EXAMPLE 4

One thousand tablets for oral use, each containing 250 mg. of essential active ingredient are prepared from the following ingredients:

| | |
|---|---|
| essential active ingredient | 250 gm. |
| dicalcium phosphate | 150 gm. |
| methylcellulose, U.S.P. (15 cps) | 6.5 gm. |
| talc | 20 gm. |
| calcium stearate | 2.5 gm. |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of hypertension in adult humans at a dose of 1 tablet administered 2 or 3 times a day.

EXAMPLE 5

One thousand two-piece hard gelatin capsules for oral use, each capsule containing 10 mg. of essential active ingredient are prepared from the following ingredients:

| | |
|---|---|
| essential active ingredient | 10 gm. |
| lactose, U.S.P. | 100 gm. |
| starch, U.S.P. | 10 gm. |
| talc | 5 gm. |
| calcium stearate | 1 gm. |

The finely powdered materials are mixed thoroughly, then filled into hard gelatin capsules of appropriate size.

A satisfactory clinical response is obtained in adults suffering from hypertension upon administration of 1 capsule 4 times a day.

EXAMPLE 6

One-piece soft elastic capsules for oral use, each containing 20 mg. of essential active ingredient are prepared in the usual manner by first dispersing the powdered active material in sufficient corn oil to render the material capsulatable.

One capsule administered 4 times a day is useful in the treatment of moderate hypertension and anxiety in adult humans.

EXAMPLE 7

An aqueous oral preparation containing in each teaspoonful (5 ml.) 25 mg. of essential active ingredient hydrochloride is prepared from the following:

| | |
|---|---|
| essential active ingredient hydrochloride | 50 gm. |
| methylparaben, U.S.P. | 7.5 gm. |
| propylparaben, U.S.P. | 2.5 gm. |
| saccharin sodium | 12.5 gm. |
| glycerin | 3,000 ml. |
| tragacanth powder | 10 gm. |
| orange oil flavor | 10 gm. |
| F. D. and C. orange dye | 7.5 gm. |
| deionized water, q.s. to | 10,000 ml. |

The foregoing aqueous preparation is useful in the treatment of adults for hypertension at a dose of 1 teaspoonful given 4 times a day.

EXAMPLE 8

One thousand tablets for oral administration, each containing 10 mg. of essential active ingredient and 16.2 mg. of phenobarbital are prepared from the following ingredients:

| | |
|---|---|
| essential active ingredient, micronized | 10 gm. |
| phenobarbital | 16.2 gm. |
| lactose | 150 gm. |
| starch | 15 gm. |
| magnesium stearate | 1.5 gm. |

The ingredients are thoroughly mixed and slugged. The slugs are broken down by forcing through a screen and the resulting granules are then compressed into tablets.

These tablets are useful in treating excited, hypertensive mammals such as dogs at a dose of 1 to 3 tablets daily depending on the weight of the animal and its condition.

EXAMPLE 9

A sterile aqueous suspension suitable for intramuscular injection and containing in each milliliter 100 mg. of essential active ingredient is prepared from the following ingredients:

| | |
|---|---|
| essential active ingredient | 10 gm. |
| polyethylene glycol 4000, U.S.P. | 3 gm. |
| sodium chloride | 0.9 gm. |
| polysorbate 80, U.S.P. | 0.4 gm. |
| sodium metabisulfite | 0.1 gm. |
| methylparaben, U.S.P. | 0.18 gm. |
| propylparaben, U.S.P. | 0.02 gm. |
| water for injection, q.s. to | 100 ml. |

The above sterile injectable is useful in the treatment of hypertension at a dose of 1 to 2 ml. administered daily.

EXAMPLE 10

One thousand suppositories, each weighting 2.5 gm. and containing 250 mg. of essential active ingredient, are prepared from the following ingredients:

| | |
|---|---|
| essential active ingredient | 250 gm. |
| propylene glycol | 165 gm. |
| polyethylene glycol (PEG) 4000 q.s. | 2,500 gm. |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of hypertension in mannals at a dose of 1 suppository administered rectally twice a day.

EXAMPLE 11

One thousand hard gelatin capsules for oral use, each containing 25 mg. of essential active ingredient and 25 mg. of hydrochlorothiazide are prepared from the following ingredients:

| | |
|---|---|
| essential active ingredient, micronized | 25 gm. |

-continued

| | |
|---|---|
| hydrochlorothiazide | 25 gm. |
| starch | 125 gm. |
| talc | 25 gm. |
| magnesium stearate | 1.5 gm. |

One capsule given 3 or 4 times a day is useful in the relief of moderate hypertension in adult humans.

EXAMPLE 12

Ten thousand scored tablets for oral use, each containing 25 mg. of essential active ingredient and 0.08 mg. of reserpine, are prepared from the following ingredients and using the procedure of Example 8, supra.

| | |
|---|---|
| essential active ingredient, micronized | 250 gm. |
| reserpine | 0.8 gm. |
| lactose | 1,500 gm. |
| corn starch | 500 gm. |
| talc | 500 gm. |
| calcium stearate | 25 gm. |

This combination of active materials is effective in reducing hypertension in adult humans. The dose is one-half to two tablets given 3 to 4 times a day, depending on the severity of the condition.

EXAMPLE 13 Aqueous Suspension

An aqueous suspension for oral administration is prepared by suspending the essential active ingredient at a concentration of 5 mg./ml. in an aqueous solution containing 1% of sodium carboxymethylcellulose. This suspension is used for bringing about hypotensive effects in unanesthetized normotensive rats. the rats are prepared for measuring blood pressure directly from the aorta through a chronic indwelling cannula (method of Weeks and Jones, Proc. Soc. Exptl. Biol. and Med., 104, 646, 1960). Arterial blood pressure is measured prior to and at 24 hours after oral administration of 50 mg./kg. body weight, of essential active ingredient. the result, a lowering of blood pressure, is set forth in the Table 1 below.

TABLE I

| Rat No. | Initial b.p. mmHq | b.p. Change mmHq at 24 hr. |
|---|---|---|
| 845 | 136 | −20 |
| 848 | 130 | −24 |
| 855 | 130 | −6 |
| 867 | 134 | −24 |
| average | 133 | −19 |

The data presented in table (I) illustrates the effectiveness of a compound (I) of the invention in lowering the blood pressure of a mammal. A mean pressure reduction of at least 10 mm. of mercury is considered to be indicative of effectiveness in lowering blood pressures in mammals.

EXAMPLE 14

Following the procedure of the preceding Examples 4 to 13, inclusive, similar dosage forms are prepared by substituting an equivalent amount of the other inventive compounds or their acid addition salts, such as for example 1-[p-[(4-quinolyl)amino]benzoyl]-4-methylpiperazine-4-oxide; 1-[p-[(7-chloro-4-quinolyl)amino]benzoyl]-4-butylpiperazine-4-oxide; 1-[p-[(7-chloro-4-quinolyl)amino]benzoyl]-4-benzylpiperazine-4-oxide; 1-[p-[(6-methoxy-4-quinolyl)amino]benzoyl]-4-methylpiperazine-4-oxide; 1-[p-[(5-isobutoxy-4-quinolyl)amino]benzoyl]-4-methylpiperazine-4-oxide; 1-[p-[(7-methyl-4-quinolyl)amino]benzoyl]-4-methylpiperazine-4-oxide; 1-[p-[(6-isopropyl-4-quinolyl)amino]benzoyl]-4-methylpiperazine-4-oxide; 1-[p-[[(7-trifluoromethyl)-4-quinolyl]amino]benzoyl]-4-methylpiperazine-4-oxide; 1-[p-[[(7-trifluoromethyl)-4-quinolyl]amino]benzoyl]4-isobutylpiperazine-4-oxide; 1-[p-[[(7-trifluoromethyl)-4-quinolyl]amino]benzoyl]-4-benzylpiperazine-4-oxide; 1-[p-[[(7-trichloromethyl)-4-quinolyl]amino]-4-methyl-piperazine-4-oxide; 1-[p-[(7-chloro-4-quinolyl)-N-ethylamino]benzoyl]-4-methylpiperazine-4oxide; 1-[p-[(7-chloro-4-quinolyl)-amino]benzoyl]-4-phenylpiperazine-4-oxide; 1-[p-[(7-chloro-4-quinoly)amino]benzoyl]-4-(p-chlorophenyl)piperazine-4-oxide; 1-[p-[(7-chloro-4-quinolyl)amino]benzoyl]-4-(m-methoxyphenyl)piperazine-4-oxide; 1-[p-[(7-chloro-4-quinolyl)-amino]benzoyl]-4-(o-tolyl)piperazine-4-oxide; and 1-[p-[(7-chloro-4-quinolyl)amino]benzoyl]-4-(m-trifluoromethylphenyl)piperazine-4-oxide, respectively.

We claim:

1. A pharmaceutical dosage unit form adapted to systemic administration to obtain antihypertensive and anti-anxiety effects which comprises an effective amount for said effects of a compound of the formula:

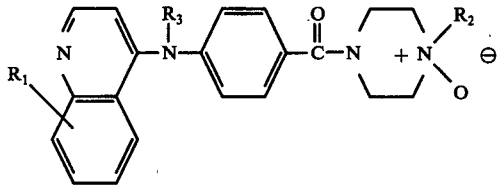

hydrates thereof and pharmaceutically acceptable acid addition salts thereof, wherein $R_1$ is halogen, lower alkyl, or trifluoromethyl; $R_2$ is selected from lower alkyl, benzyl, phenyl and phenyl substituted with one of the groups selected from halogen, lower alkyl, and trifluoromethyl; $R_3$ is hydrogen; in combination with a pharmaceutical carrier.

2. The composition of claim 1 wherein said compound is 1-[p-[(7-chloro-4-quinolyl)amino]benzoyl]-4-methylpiperazine-4-oxide.

3. The composition of claim 3 wherein said compound is 1-[p-[[(7-trifluoromethyl)-4-quinolyl]amino]-benzoyl]-4-methylpiperazine-4-oxide hydrate.

4. A method of treating hypertension in a mammal which comprises administering systemically to said mammal a pharmaceutical dosage unit form supplying an effective amount for antihypertensive effect of a compound of the formula:

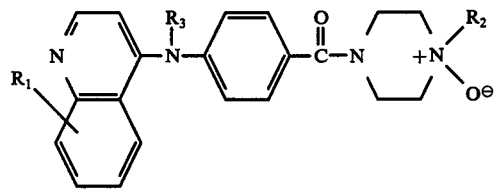

hydrates thereof and pharmaceutically acceptable acid addition salts thereof wherein $R_1$ is halogen, lower alkyl, or trifluoromethyl; $R_2$ is selected from lower alkyl, benzyl, phenyl and phenyl substituted with one of the groups selected from halogen, lower alkyl, and trifluoromethyl; $R_3$ is hydrogen.

5. The method of claim 4 wherein the amount of compound administered daily is within the range of from about 0.5 mg. per kg. to about 25 mg. per kg. of weight of said mammal.

6. The method of claim 4 wherein the compound is 1-[p-[[(7-trifluoromethyl)-4-quinolyl]amino]benzoyl]-4-methylpiperazine-4-oxide hydrate.

7. The method of claim 4 wherein the compound is 1-[p-[(7-chloro-4-quinolyl)amino]benzoyl]-4-methylpiperazine-4-oxide.

8. The method of claim 4 wherein said mammal is a human.

9. A method of treating hypertension in a mammal which comprises administering to said mammal an effective amount of a compound of the formula:

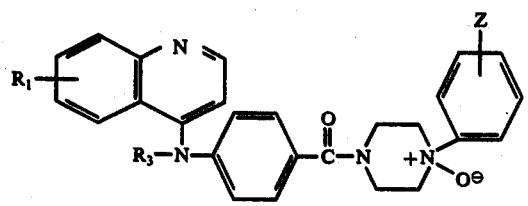

and the pharmaceutically acceptable acid addition salts thereof, wherein $R_1$ is halogen, lower alkyl, or trifluoromethyl; $R_3$ is hydrogen; and Z is hydrogen, halogen, lower alkyl, or trifluoromethyl.

* * * * *

UNITED STATES PATENT AND TRADEMARK OFFICE
CERTIFICATE OF CORRECTION

PATENT NO. : 4,057,633

DATED : November 8, 1977

INVENTOR(S) : Charles E. Coverdale and Louis L. Skaletzky

It is certified that error appears in the above-identified patent and that said Letters Patent are hereby corrected as shown below:

Column 3, line 51: "cholor-" should read -- chloro- --.
Column 4, line 29: "oromo" should read -- bromo --.
Column 6, line 5: "preferably" should read -- preferable --.
Column 6, line 39: "quanethidine" should read -- guanethidine --.
Column 7, line 50: "benzoyly" should read -- benzoyl --.
Column 7, line 51: "quinloyl" should read -- quinolyl --.
Column 7, line 51: "benzoly" should read -- benzoyl --.
Column 7, line 54: "benzoly" should read -- benzoyl --.
Column 7, line 64: ")amino]amino]benzoly]-" should read -- )amino]benzoyl]- --.
Column 7, line 65: "benzolyl" should read -- benzoyl --.
Column 7, line 67: "benzoly" should read -- benzoyl --.
Column 7, line 68: "ispropyl" should read -- isopropyl --.
Column 8, line 2: "isobutypiperazine" should read -- isobutylpiperazine --.
Column 8, line 4: "1-[-" should read -- 1-[p- --.
Column 8, line 5: "benzoly" should read -- benzoyl --.
Column 8, line 6: "benzoly" should read -- benzoyl --.
Column 8, line 11: "benzoly" should read -- benzoyl --.
Column 8, line 14: "-4(" should read -- -4-( --.
Column 8, line 23: "quniolyl" should read -- quinolyl --.
Column 8, line 60: "benzoly" should read -- benzoyl --.
Column 11, line 40: "ingredient. the" should read -- ingredient. The --.

UNITED STATES PATENT AND TRADEMARK OFFICE
CERTIFICATE OF CORRECTION

PATENT NO. : 4,057,633
DATED : November 8, 1977
INVENTOR(S) : Charles E. Coverdale and Louis L. Skaletzky It is certified that error appears in the above-identified patent and that said Letters Patent are hereby corrected as shown below:

Column 12, line 10: "amino]-4-" should read -- amino]benzoyl]-4- --.
Column 12, Claim 3, line 1: "claim 3" should read -- claim 1 --.

Signed and Sealed this

Eighth Day of September 1981

[SEAL]

Attest:

GERALD J. MOSSINGHOFF

Attesting Officer    Commissioner of Patents and Trademarks